United States Patent [19]

McDonald

[11] 4,378,010
[45] Mar. 29, 1983

[54] MEDICAL SUPPORT AND PROTECTOR

[75] Inventor: Eleanor McDonald, Clay Center, Kans.

[73] Assignee: V.M.G.E. Research & Development Corp., Clay Center, Kans.

[21] Appl. No.: 252,896

[22] Filed: Apr. 10, 1981

[51] Int. Cl.[3] .......................... A61F 13/00; A61F 5/40
[52] U.S. Cl. .................................... 128/168; 128/158; 128/DIG. 26
[58] Field of Search ...................... 128/772, 79, 82, 98, 128/138 R, 157–162, 168, 171, 294–295, DIG. 26

[56] References Cited

U.S. PATENT DOCUMENTS

| | | |
|---|---|---|
| 1,057,693 | 4/1913 | Ware . |
| 1,074,147 | 9/1913 | Whitlock . |
| 1,193,432 | 8/1916 | Schwarzer .......................... 128/161 |
| 1,208,758 | 12/1916 | Deutsch . |
| 2,046,094 | 6/1936 | Schmidt . |
| 2,320,736 | 6/1943 | Nevins . |
| 2,684,673 | 7/1954 | Lerman . |
| 3,225,761 | 12/1965 | Swensen . |
| 3,238,939 | 3/1966 | Stubbs . |
| 3,895,629 | 7/1975 | Snyder . |
| 4,059,105 | 11/1977 | Cutruzzula et al. . |
| 4,088,136 | 5/1978 | Hasslinger et al. . |
| 4,165,748 | 8/1979 | Johnson . |
| 4,187,851 | 2/1980 | Hauser . |

OTHER PUBLICATIONS

"Surgical Nursing", Felter, West and Zetsche, Fifth Edition, 1950, pp. 332 and 333.
"Testbook of Medical–Surgical Nursing", Brenner & Suddarth, Anchoring the Indwelling Catheter", pp. 630–631, Figures 26–5.
"Urology Tips", Abbott Laboratories, Taping of Male, Jun. 1975.

Primary Examiner—C. Fred Rosenbaum
Attorney, Agent, or Firm—Oblon, Fisher, Spivak, McClelland & Maier

[57] ABSTRACT

A penis-scrotum-catheter supporting and protecting apparatus for the male genitalia includes a mesh pouch for retaining, enclosing and supporting the male genitalia. The mesh pouch includes an upper edge portion defining an opening for accommodating the penis. Adhesive elements are provided for securing the upper and lower portions of the mesh pouch to the human body. A flexible separable strip is attached to the upper portion of the mesh pouch for adjustably joining first and second adjacent upper portions of the mesh pouch.

7 Claims, 2 Drawing Figures

MEDICAL SUPPORT AND PROTECTOR

BACKGROUND OF THE INVENTION

1. Field of the Invention

This invention relates generally to a protective apparatus for the management of male genitalia, and more particularly to an apparatus which provides suspensory and dressing support for the scrotum as well as maintenance of a catheter in an upright cephalad position for operative and post operative observation.

2. Description of the Prior Art

In the field of medicine and in the practice of surgery, numerous problems have arisen in which the male genitals need support, retention and protection. Attempts to realize these objectives have been tried by the use of tape, towels and by the use of instruments. However, such attempts have been less than successful in that the genitals have not been retained securely, or the patient has experienced unnecessary pain and discomfort. Another encountered problem has been the development of a fistula at the peno-scrotal juncture, caused by allowing the catheter to fall in a downward position, thereby applying pressure on the urethra. In addition, numerous attempts to keep intact the dressing and/or hot and cold applications to the scrotum have been met with poor results.

A suspensory device generally directed to the above mentioned problems is shown by Whitlock in U.S. Pat. No. 1,074,147, which discloses an inflatable scrotum supporter including adjustable waste and leg straps for securing to the supporter to the body. The adjustable straps must be buckled at at least three points which is both time consuming and cumbersome. In addition, Whitlock provides no support for the penis in an upright position and makes no provision for securing a catheter to the body.

Another suspensory device is disclosed by Deutche in U.S. Pat. No. 1,208,758 wherein a pouch or sack is suspended from adjustable straps which are connected to an adjustable waist band. Buckles are provided for the adjustment of the waist band and sack, however, no provision is made for penis or catheter support or for the adjustment of such support.

While fasteners for catheters such as that shown by Hasslinger et al in U.S. Pat. No. 4,088,136 have been disclosed, no such device has been found to be incorporated within a penis-scrotum suspensory similar to that of the present invention. In addition, adhesive securing devices have been disclosed which support a needle or catheter against the body, such as disclosed by Cutruzzula et al in U.S. Pat. No. 4,059,105, however, no incorporation without a suspensory device is disclosed.

Thus, there exists a need for a penis, scrotum catheter protector which is easy to apply, free from cumbersome belts and fasteners, and which provides support for the penis, scrotum and indwelling catheter if used, so as to maximize patient comfort, minimize the incidence of fistula formation, and realize the numerous objectives discussed below.

SUMMARY OF THE INVENTION

Accordingly, this invention has been made to overcome the problems described above, and has therefore an object to provide an apparatus for retaining, protecting and supporting the male penis, scrotum and indwelling catheter, if used. This apparatus can be used in multiple positions such as the supine, prone, lithotomy, lateral and erect positions. Such use is of particular value to many operative and medical procedures, particularly those in which clear access to the rectal area is required.

A further object is to facilitate the surgeon's work by eliminating any interference with or obstruction to the surgery thereby providing operation site accessability through the retraction of the male genitals.

Yet another object is to permit the visual examination of the penis during and after surgery as well to secure any necessary dressing in place.

A still further object of the invention is to provide post-operative comfort and to maintain the penis in an upright or cephalad position for the avoidance of abcess or fistule formation, especially at the peno-scrotal juncture.

Another object is to provide an easy-to-apply fastening device for securing the protector to the body without employing body member encircling fasteners such as belt and buckle devices utilized by the prior art.

Another object is to maximize patient comfort and support by providing an elastic periphery about the mesh pouch protector to snugly support the male genitalia.

The foregoing and other objects are achieved according to the present invention by the provision of an apparatus for the support of the male genitalia, which includes an expandable mesh pouch with an elastic periphery for snugly retaining the penis and scrotum under various anatomical body positions. Upper and lower elastic adhesive strips are employed to secure the protector to the body without encircling the waist or legs. At least one separable Velcro strip is attached to the upper portion of the mesh pouch to provide both adjustment for the pouch and support for the penis. The separable Velcro strip additionally bridges the upper corners of the pouch to form a semicircular opening through which the penis may be examined. Attached to each upper elastic adhesive strip is a Velcro separable strip for securing and supporting any drainage tubing present.

BRIEF DESCRIPTION OF THE DRAWINGS

Various other objects, features and attendant advantages of the present invention will be more fully appreciated as the same becomes better understood from the following detailed description when considered in connection with the accompanying drawings, in which like reference characters designate like or corresponding parts through the several views and wherein.

DETAILED DESCRIPTION OF THE PREFERRED EMBODIMENT

Figure 1:
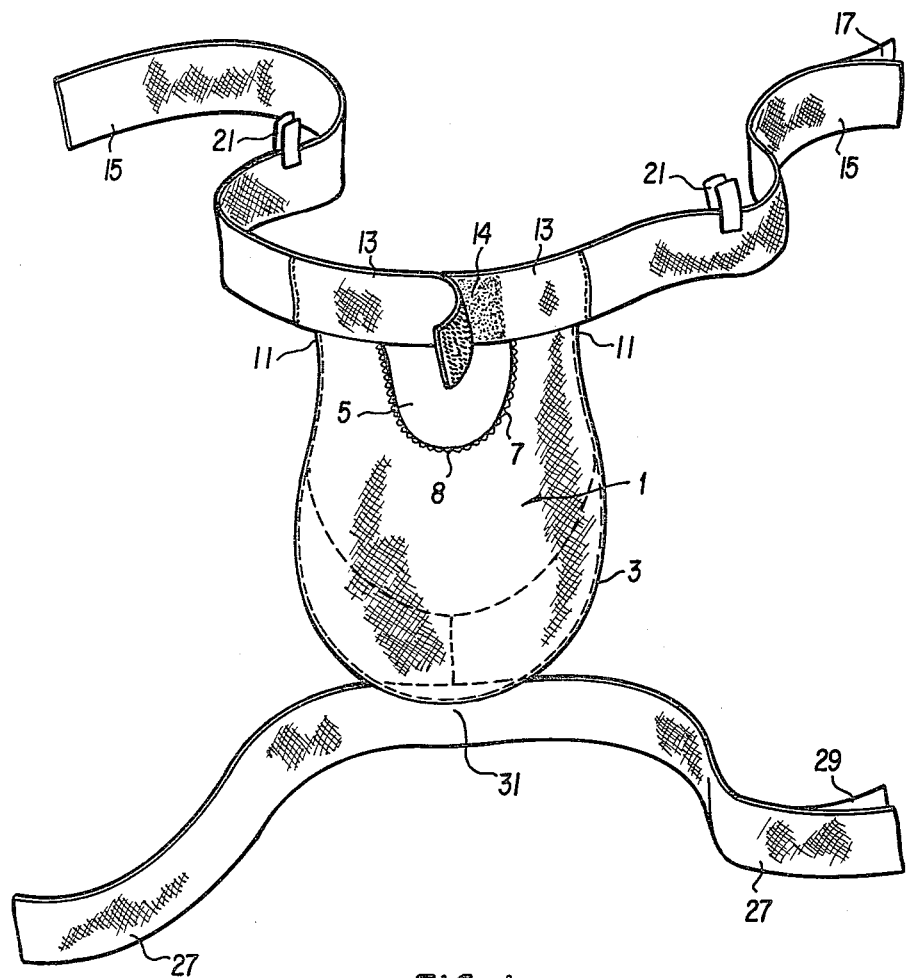
FIG. 1 is a front elevation view of a preferred embodiment of the medical support and protector.

The apparatus developed in accordance with the present invention will now be described in conjunction with the accompanying FIG. 1, within which, for example, an expandable mesh pouch 1, with an elastic periphery 3 of such size to retain, enclose and support the dependent member and such dressings and/or hot or cold applications as are deemed necessary is disclosed.

The semi-circular opening 5 on the upper edge portions 7 of the pouch 1 accommodates the penis 9 in an anatomically correct position so as to eliminate the peno-scrotal angle and prevent formation of fistulae. In addition, the semi-circular opening 5 permits visual examination of the penis above the lower arcuate boundary 8.

The opening 5 is joined at the upper surface portions 11 by a separable strip 13 fabricated from a material such as Velcro, which may be applied either over or under the penis in the upright or cephalad position. End portions 14 of the separable strip 13 include mating securing surfaces for fastening and joining the separable strip. The separable strip 13 is attached at both upper surface sections 11 of the mesh sack 1 to an elastic adhesive material strip 15 with a peelable backing 17 which adheres to left and right lower surface portions 19 of the abdomen without encircling the waist.

Separable strips 21 attached to each elastic strip 15 may be provided to secure and support any necessary drainage tubing 23. An elastic adhesive strip 27 with a peelable backing 29 is attached to a lower or posterior surface portion 31 of the mesh pouch 1. Adhesive strip 27 secures the mesh pouch 1 to the scrotal-perineal juncture 33 by adhereing to the left and right thigh surface portions 35 without encircling the thighs.

Figure 2:
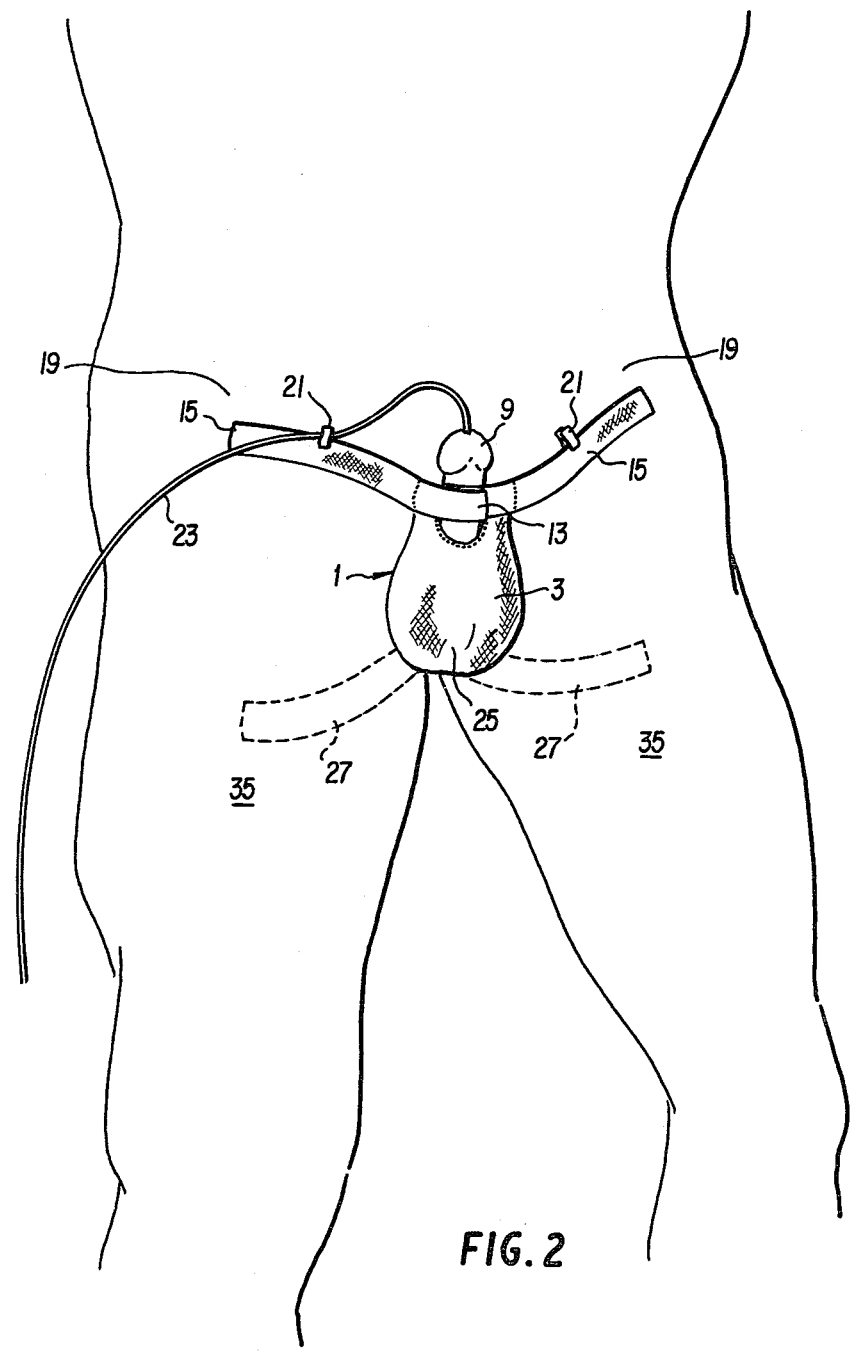
FIG. 2 is a front elevation view of the mid portion of the human body illustrating the use of the present invention in the upright position.

Referring to FIG. 2, the apparatus is applied by placing the mesh pouch 1 around the scrotum 25 so as to encircle and support the scrotum while maintaining the penis 9 in the upright or cephalad position. The adhesive strips 15 are then secured outwardly to the right and left of the mesh sack 1 to the body without encircling the waist after removal of the peelable backing 17.

The separable strip 13 is then fastened either above or over the penis so as to join the upper surfaces 11 of the mesh sack 1 such that the penis 9 is visible through the opening 5. If drainage tubing 23 is present, the separable strip 13 is fastened over the tubing 23 at the point at which the tubing exits from the penis 9 or directly over the penis so as to securely anchor and immobilize the tubing against the lower portion of the abdomen 19. The peelable backing 29 is then removed from the adhesive strip 27. The adhesive strip 27 is then applied outwardly to the thighs without encircling the thighs to complete the application.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A supporting and protecting apparatus for the male genitalia comprising:
    a mesh pouch;
    said mesh pouch further comprising upper edge portions defining an opening;
    said mesh pouch further comprising first and second upper surface portions and a lower surface portion;
    adhesive means adapted for securing said upper and lower portions of said mesh pouch to the human body such that said mesh pouch retains, encloses, accommodates and supports said male genitalia; and
    at least one flexible separable strip attached to said first upper surface portion of said mesh pouch for adjustably joining said second upper surface portion of said mesh pouch.

2. The apparatus of claim 1 wherein said adhesive means comprise:
    at least one elastic adhesive material strip attached to said first and second upper portions of said mesh pouch adapted for securing said mesh pouch to a lower abdominal surface; and
    further comprising at least one elastic adhesive material strip attached to said lower portion of said mesh pouch adapted for securing said pouch to a thigh surface.

3. The apparatus of claim 2 further comprising a Velcro separable strip attached to said at least one elastic adhesive material strip attached to said first and second upper portions of said mesh pouch adapted for securing and supporting drainage tubing.

4. The apparatus of claim 1 wherein said at least one flexible separable strip comprises a first and second separable strip attached to said first and second upper surface portions, respectively, at one end thereof and each having an end portion opposite said one end, and means mounted on each of said opposite end portions for securing said opposite end portions together.

5. The apparatus of claim 1 wherein said upper edge portions form a lower arcuate boundary and wherein said at least one flexible separable strip forms an upper boundary such that a semicircular opening is defined for observation of the penis.

6. A supporting and protecting apparatus for the male genitalia comprising:
    a mesh pouch;
    said mesh pouch further comprising upper edge portions defining an opening;
    said mesh pouch further comprising first and second upper surface portions and a lower surface portion; and
    adhesive means adapted for securing said upper and lower portions of said mesh pouch to the human body such that said mesh pouch retains, encloses, accommodates and supports said male genitalia;
    wherein said adhesive means further comprise elastic adhesive material strips such that said strips are secured to the body without encircling any body member within said strips.

7. The apparatus of claim 1 or 6, said mesh pouch further comprising an elastic periphery.

* * * * *